United States Patent
Frost

(10) Patent No.: US 6,363,617 B1
(45) Date of Patent: Apr. 2, 2002

(54) GUARD FOR CAST CUTTER

(76) Inventor: Terry Frost, R.R. 1, Site 16, Comp. 11, Golden, British Columbia (CA), V0A 1H0

( * ) Notice: Subject to any disclaimer, the term of this patent is extended or adjusted under 35 U.S.C. 154(b) by 0 days.

(21) Appl. No.: 09/545,468

(22) Filed: Apr. 7, 2000

(51) Int. Cl.$^7$ ............................................. B23D 47/02
(52) U.S. Cl. ............................. 30/370; 30/289; 30/293; 30/390
(58) Field of Search .................... 30/370, 390, 388, 30/124, 293, 286, 373, 289

(56) References Cited

U.S. PATENT DOCUMENTS

| | | | |
|---|---|---|---|
| 1,737,552 A | * 12/1929 | Altman et al. | 30/370 |
| 1,813,693 A | * 7/1931 | Balinski et al. | 30/370 |
| 1,942,766 A | * 1/1934 | O'Banion | 30/289 |
| 2,217,923 A | * 10/1940 | Silverman | 30/370 |
| 2,617,186 A | * 11/1952 | Pickles | 30/370 |
| 2,698,997 A | * 1/1955 | King et al. | 30/370 |
| 4,166,317 A | 9/1979 | Bettcher | 30/276 |
| 4,188,943 A | 2/1980 | Sjostrand | 602/9 |
| 4,233,736 A | 11/1980 | Duggins et al. | 30/293 |
| 4,316,323 A | 2/1982 | Kirk | 30/124 |
| 4,318,224 A | 3/1982 | Getts | 30/377 |
| 4,324,044 A | 4/1982 | Shahinian, Jr. | 30/294 |
| 4,421,111 A | 12/1983 | Rothman | 606/105.5 |
| 4,432,264 A | 2/1984 | Scott | 83/835 |
| 4,515,055 A | 5/1985 | Scott | 83/835 |
| 4,520,815 A | 6/1985 | Marinoff | 606/166 |
| 4,625,405 A | 12/1986 | Hudnutt et al. | 30/370 |
| 4,637,391 A | 1/1987 | Schlein | 606/172 |
| 4,680,083 A | 7/1987 | Kashiwaba | 156/510 |
| 4,796,502 A | 1/1989 | Anderson | 83/834 |
| 4,887,598 A | 12/1989 | Berke | 606/180 |
| 4,955,890 A | 9/1990 | Yamamoto et al. | 606/108 |
| 4,976,034 A | * 12/1990 | Whiteman | 30/370 |
| 5,020,226 A | 6/1991 | Chabbert | 30/390 |
| 5,115,567 A | 5/1992 | Yang et al. | 606/172 |
| 5,218,787 A | 6/1993 | Rice | 451/229 |
| 5,303,471 A | 4/1994 | Liberatoscioli | 30/122 |
| 5,309,407 A | 5/1994 | Sehr et al. | 367/96 |
| 5,439,472 A | 8/1995 | Evans et al. | 606/176 |
| 5,569,285 A | 10/1996 | Webb | 606/180 |
| 5,601,584 A | 2/1997 | Obagi et al. | 606/172 |
| 5,620,453 A | 4/1997 | Nallakrishnan | 606/166 |
| 5,653,033 A | 8/1997 | McDowell | 30/390 |
| 5,662,436 A | 9/1997 | Bishop | 407/35 |
| 5,707,276 A | 1/1998 | Holko et al. | 451/356 |
| 5,724,875 A | 3/1998 | Meredith et al. | 83/397 |
| 5,766,198 A | 6/1998 | Li | 606/172 |
| 5,769,866 A | 6/1998 | Frantzen | 606/167 |
| 5,809,985 A | 9/1998 | Kingsley et al. | 125/13.01 |
| 5,810,448 A | 9/1998 | Kingsley et al. | 299/39.3 |

* cited by examiner

*Primary Examiner*—Hwei-Slu Payer
(74) *Attorney, Agent, or Firm*—Christensen O'Connor Johnson Kindness PLLC

(57) ABSTRACT

A guard for a cast cutter includes a first member securable to a cast cutter and a second member securable to a guard member. The second member is freely movable relative to the first member during operation along a support axis. Stops limiting movement in either direction along the support axis. This cast cutter guard has only one setting which accommodates variations thickness. Pressure exerted upon the cast cutter during operation results in movement of the second member relative to the first member, rather than pressure upon the injured area.

7 Claims, 4 Drawing Sheets

GUARD FOR CAST CUTTER

FIELD OF THE INVENTION

The present invention relates to a guard for a cast cutter and, in particular, a cast cutter that utilizes a rotary cutting blade.

BACKGROUND OF THE INVENTION

Medical staff place a cast over a broken limb of a patient to protect the area of the break and maintain proper bone positioning during healing. A layer of fabric is first placed over the patient's limb. Plaster is then placed over the layer of fabric. The plaster hardens to provide both support for the injured area and a protective layer.

When the cast is to be removed it must be cut away using cast cutters. A common form of cast cutter used in many hospitals uses a rotary blade. Great care must be when a rotary blade cast cutter is used. If penetration of the rotary blade is too deep, the patient will receive a cut from the blade. The blade becomes heated during cutting, so even if the blade does not cut the patient, the patient can receive a burn if the blade is brought too close to the skin. The rotary cutter blades are durable enough to withstand numerous uses. However, when the blade are used on multiple patients there is a danger that they may become instruments for the spread of infectious diseases.

An obvious solution to the problem of cuts from the cast cutter is to provide some form of guard. U.S. Pat. Nos. 4,625,405 and 5,020,226 both illustrate cast cutters with hook like guards that maintain a cutting blade a constant distance from a patient's skin. Due to some inherent disadvantages, these types of guards have not gained favour with medical staff. One disadvantage is that casts come in a variety of thicknesses. As a result, there is a need to adjust the depth of the guard from cast to cast, which is time consuming. Another disadvantage is that casts tend to be irregular in thickness. As a result there is a need to adjust the depth of the guard during the cutting of the cast. A further problem is that the guard tends to exert pressure upon the injured area. This causes the patient discomfort, especially when the cast is being cut in the proximity of stitches or sutures.

SUMMARY OF THE INVENTION

What is required is an alternative configuration of guard for a cast cutter.

According to one aspect of the present invention there is provided a guard for a cast cutter which includes a first member securable to a cast cutter and a second member securable to a guard member. The second member is freely movable relative to the first member during operation along a support axis. A first stop limits movement of the second member toward the first member along the support axis. A second stop limits movement of the second member away from the first member along the support axis.

The cast cutter guard, as described above, overcomes the disadvantages inherent in prior art cast cutter guards. The second member moves freely relative to the first member along the support axis during operation. This provides an advantage to medical staff, as the cast cutter guard has only one setting, which accommodates any thickness of cast as well as variations in the thickness of an individual cast. This provides an advantage to the patient, as the pressure exerted by the medical staff upon the cast cutter translates into movement of the second member relative to the first member; rather than pressure upon the injured area.

Once the teaching of the present invention of free movement of second member relative to the first member, rather than fixed guard positioning, is understood; there are a number of different physical structures to apply this teaching. The cast cutter guard that will hereinafter be described is merely a preferred one of a number of alternative configurations.

Once the teachings of the present invention are understood, it is possible for a manufacturer of a cast cutter to build this form of cast cutter guard into the cast cutter during manufacture. According to another aspect of the invention there is provided a combination of a cast cutter with a cast cutter guard. As this type of cast cutter guard is best suited for rotary blade cast cutters, the cast cutter includes a body with a rotary cutting blade rotating about a rotational axis. The cast cutter guard, as described above, has a first member positioned on the body of the cast cutter and a second member carrying a guard member. The second member is freely movable relative to the first member during operation along a support axis substantially perpendicular to the rotational axis. The first stop limits movement of the second member toward the first member along the support axis to maintain the guard member spaced outwardly a safe distance from a peripheral edge of the rotary cutting blade. The second stop limits movement of the second member away from the first member along the support axis to prevent separation of the second member from the first member.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
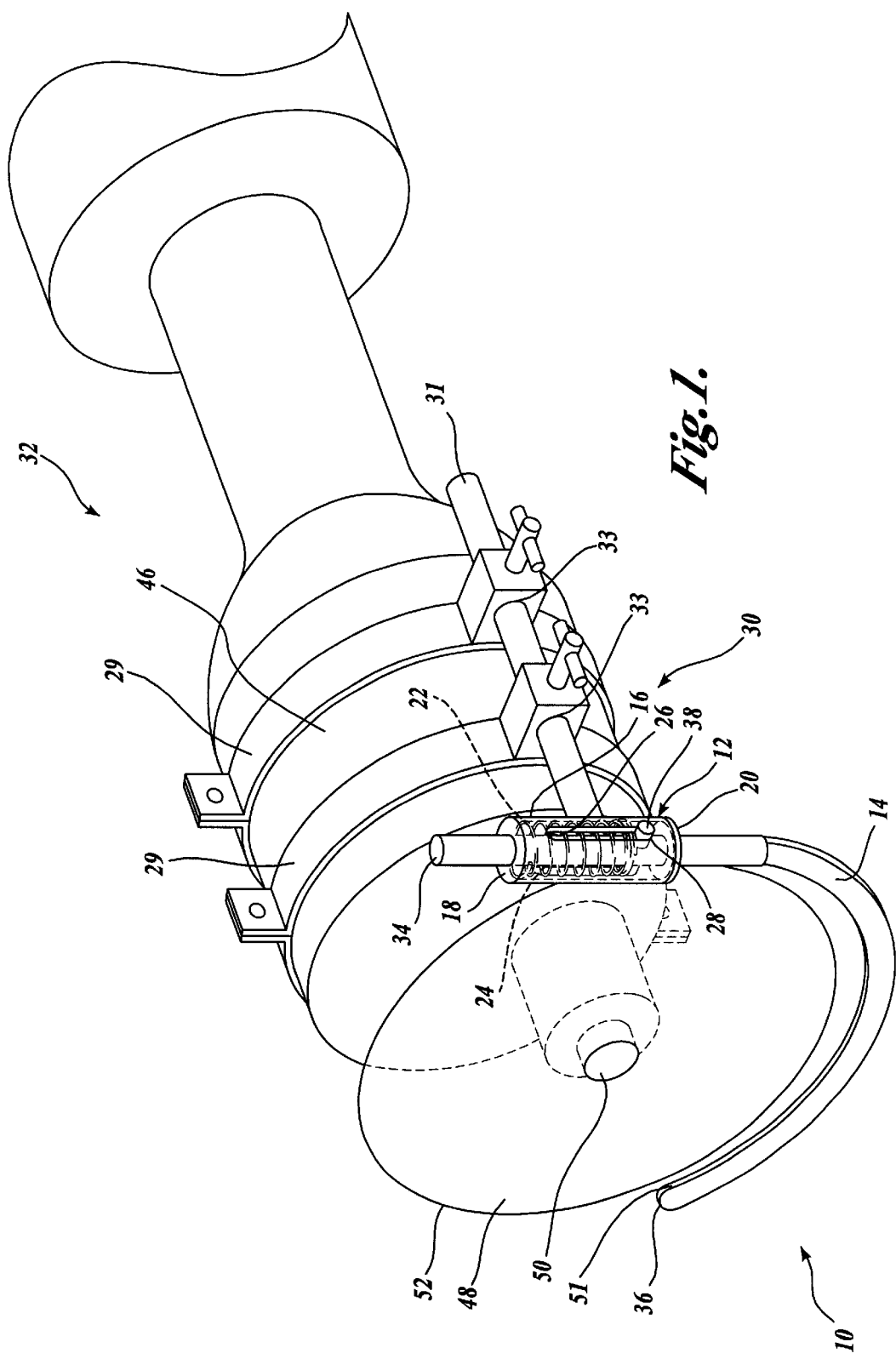
FIG. 1 is a perspective view of a cast cutter guard constructed in accordance with the teachings of the present invention positioned on a rotary blade cast cutter.

The preferred embodiment, a guard for a cast cutter generally identified by reference numeral 10, will now be described with reference to FIGS. 1 through 6.

Figure 6:
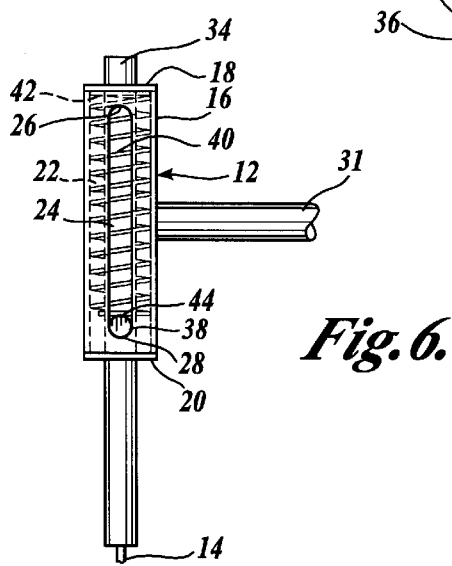
FIG. 6 is a detailed rear elevation view of the first stop and the second stop of the cast cutter guard as illustrated in FIG. 4.

Referring to FIG. 1, cast cutter guard 10 includes a first member 12 and a second member 14. Referring to FIG. 6, first member 12 has a peripheral sidewall 16, a first end 18, and a second end 20. An interior bore 22 extends between first end 18 and second end 20. A pair of opposed guide slots 24 extend through peripheral sidewall 16 to interior bore 22. Each of guide slots 24 has a first end 26 and a second end 28. Referring to FIG. 1, a mounting bracket, generally indicated by reference numeral 30, is attached to first member 12 by a mounting rod 31, whereby first member 12 is securable to a cast cutter 32. Mounting bracket 30 has two bands 29 which clamp around cast cutter 32. Mounting rod 31 passes through friction fitting apertures 33 on bands 29 of mounting bracket 30. Mounting rod 31 is telescopically movable relative to mounting bracket 30, in order to adapt to various makes and models of cast cutter 32.

Figure 4:
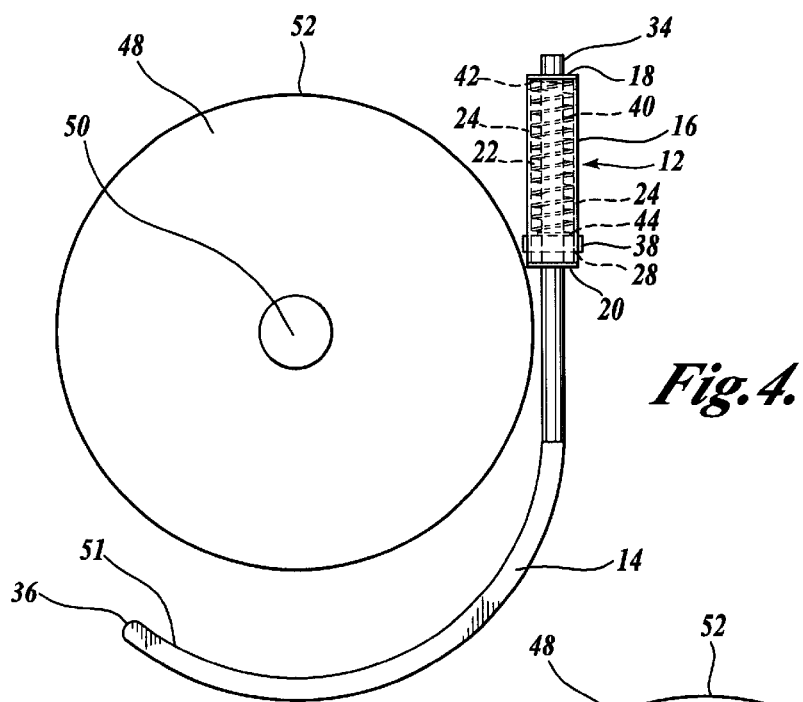
FIG. 4 is a detailed end elevation view of the cast cutter guard positioned on the rotary blade cast cutter illustrated in FIG. 1, with second member a maximum distance from the first member as determined by the second stop.
Figure 5:
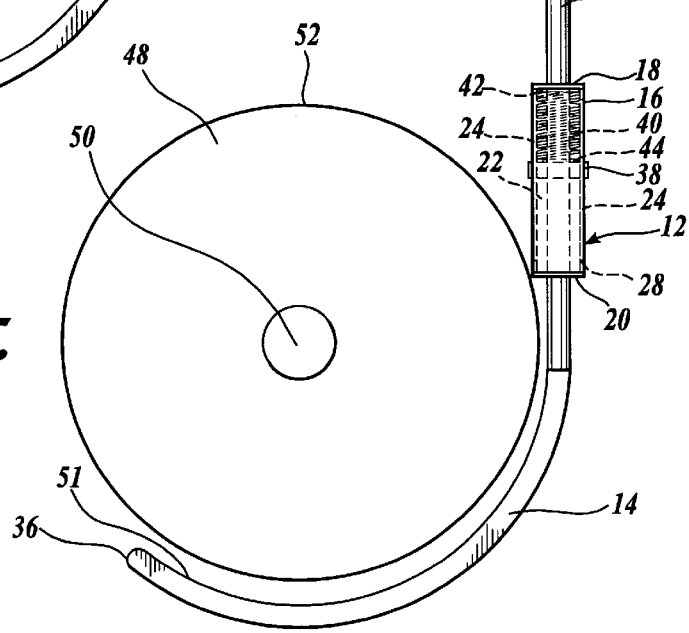
FIG. 5 is a detailed end elevation view of the cast cutter guard positioned on the rotary blade cast cutter illustrated in FIG. 1, with second member a minimum distance from the first member as determined by the first stop.

"J" shaped second member 14 has a first end 34 and a second end 36. First end 34 is telescopically received in interior bore 22 of first member 12. Second end 36 of second member 14 serves as a guard member. Second member 14 has opposed radial pins 38 that engage guide slots 24 of first member 12. Second member 14 is freely movable relative to first member 12 during operation along a support axis defined by interior bore 22 of first member 12. Referring to FIG. 5, first end 26 of guide slots 24 serves as a first stop, whereby movement of second member 14 toward first member 12 along the support axis provided by interior bore 22 is limited. Referring to FIG. 4 and 6, second end 28 of guide slots 24 serves as a second stop, whereby movement of second member 14 away from first member 12 along the support axis defined by interior bore 22 is limited. A spring 40 is disposed within interior bore 22 of first member 12. Spring 40 biases second member 14 away from first member 12. Spring 40 has a first end 42 that bears against first end 18 of first member 12 and a second end 44 that bears against radial pins 38 of second member 14.

Figure 2:
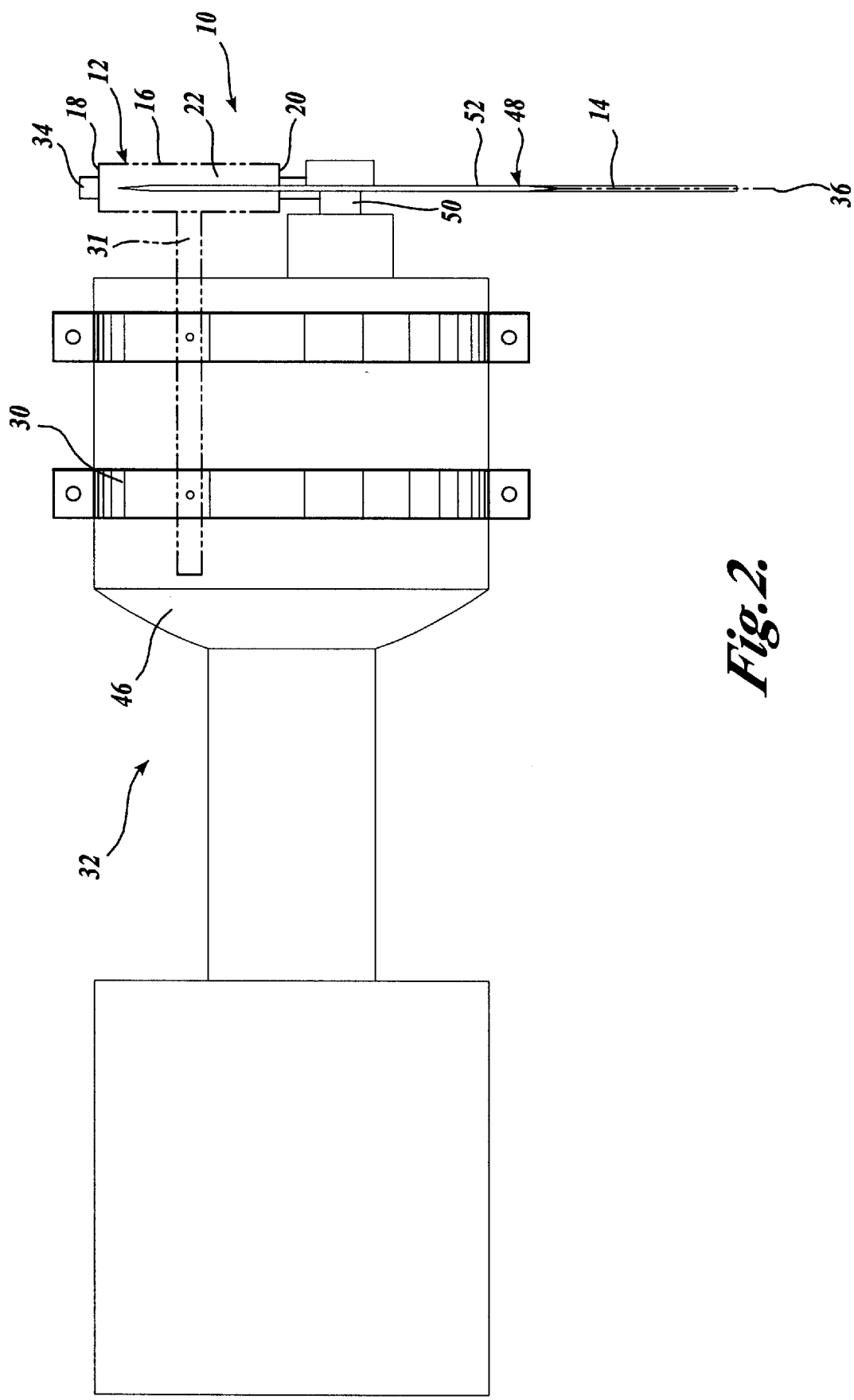
FIG. 2 is a front elevation view of the cast cutter guard positioned on the rotary blade cast cutter illustrated in FIG. 1.
Figure 3:
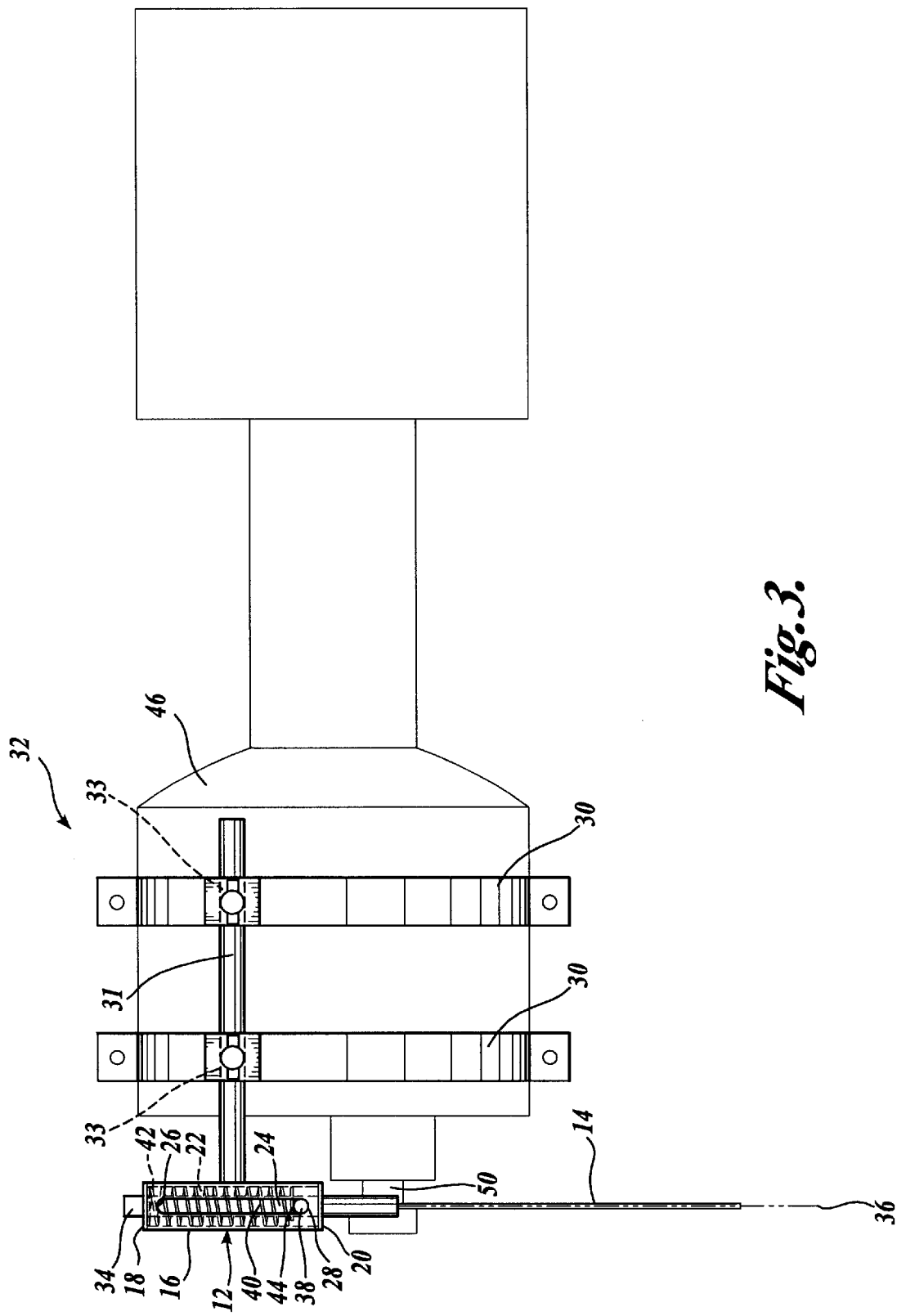
FIG. 3 is a rear elevation view of the cast cutter guard positioned on the rotary blade cast cutter illustrated in FIG. 1.

Referring to FIGS. 1 through 6, the use and operation of cast cutter guard 10 will now be described in relation to a cast cutter 32. Referring to FIG. 1, cast cutter 32 includes a body 46 with a rotary cutting blade 48 rotating about a rotational axis defined by a drive shaft 50. Mounting bracket 30 is attached to cast cutter 32. Cast cutter guard 10 as described above is attached to cast cutter 32 as will now be described. First member 12 of cast cutter guard 10 is rigidly connected to mounting rod 31. Mounting rod 31 passes through friction fitting apertures 33 on bands 29 of mounting bracket 30. The support axis defined by interior bore 22 of first member 12 is substantially perpendicular to the rotational axis defined by drive shaft 50, as illustrated in FIGS. 4 and 5. Friction fitting apertures 33 permit mounting rod 31 to be moved to adjust the positioning of first member 12 relative to mounting bracket 30. Prior to use first member 12 is moved relative to cast cutter 32 so that second member 14 is substantially coplanar with rotary cutting blade 48, as illustrated in FIGS. 2 and 3. First stop 26 limits movement of second member 14 toward first member 12 along the support axis to maintain an inner edge 51 of guard member 14 spaced outwardly a safe distance from a peripheral edge 52 of rotary cutting blade 48, as illustrated in FIG. 5. Second stop 28 limits movement of second member 14 away from first member 12 along the support axis to prevent separation of second member 14 from first member 12, as illustrated in FIG. 4.

When a cast is to be cut, second end 36 of second member 14 is inserted between the cast and the patient. Cast cutter 32 is started, and peripheral edge 52 of rotary cutting blade 48 is brought into engagement with the cast by applying sufficient pressure upon cast cutter 32 to compress spring 40. When a thicker section of the cast is engaged, the separation of peripheral edge 52 of rotary cutting blade 48 from inner edge 51 of second member 14 is initially increased by reducing the pressure on cast cutter 32. Spring 40 expands thereby biasing second member 14 away from first member 12. Second stop 28 prevents second member from separating from first member 12. The separation of peripheral edge 52 of rotary cutting blade 48 from inner edge 51 of second member 14 is subsequently reduced as the thickness, or the remaining thickness, of that part of the cast is reduced. First stop 26 prevents rotary cutting blade 48 from contacting second member 14 or the patient. A distance is always maintained to avoid the patient receiving a burn as a result of heat generated by rotary cutting blade 48. When a thinner part of the cast is to be cut, the separation of peripheral edge 52 of rotary cutting blade 48 is reduced by applying sufficient pressure on cast cutter 32 to compress spring 40 until said rotary cutting blade 48 engages the cast. Regardless of the thickness of the cast, whenever pressure is exerted to force rotary cutting blade 48 into engagement with the cast, the pressure exerted is absorbed by spring 40. This avoids placing undue pressure upon the injured portion of the patient and, in particular, areas where there are stitches or sutures.

It will be apparent to one skilled in the art that the manner of relative movement of first member and second member provides numerous advantages to cast cutter guard 10. Relative movement enables cast cutter guard 10 to accommodate any thickness of cast, and variations in thickness found within an individual cast. Relative movement means that any pressure exerted to force rotary cutting blade into cast, does not result in equal pressure being exerted by cast cutter guard 10 against the injured person.

It will be apparent to one skilled in the art that modifications may be made to the illustrated embodiment without departing from the spirit and scope of the invention as hereinafter defined in the claims.

What is claimed is:

1. A guard for a cast cutter, comprising:

a first member having a peripheral sidewall, a first end, a second end, an interior bore that extends between the first end and the second end and a pair of opposed guide slots that extend through the peripheral sidewall to the interior bore, each of the guide slots having a first end and a second end;

a mounting bracket attached to the first member, whereby the first member is securable to a cast cutter;

a "J" shaped second member having a first end and a second end, the first end of the second member being telescopically received in the interior bore of the first member, the second end of the second member serving as a guard member, the second member having opposed radial pins that engage the guide slots of the first member, the second member being freely movable relative to the first member during operation along a support axis defined by the interior bore of the first member;

the first end of the guide slots serving as a first stop, whereby movement of the second member toward the first member along the support axis is limited;

the second end of the guide slots serving as a second stop, whereby movement of the second member away from the first member along the support axis is limited; and a spring disposed within the interior bore of the first member biasing the second member away from the first member, the spring having a first end that bears against the first end of the first member and a second end that bears against the radial pins of the second member.

2. A guard for a cast cutter, comprising:

a first member having a peripheral sidewall, a first end, a second end, an interior bore that extends between the first end and the second end and a pair of opposed guide tracks in the peripheral sidewall, each of the guide tracks having a first end and a second end;

a mounting bracket attached to the first member, whereby the first member is securable to a cast cutter;

a second member having a first end and a second end, the first end of the second member being telescopically received in the interior bore of the first member, the second end of the second member carrying a guard member, the second member having opposed radial members that engage the guide tracks of the first member, the second member being freely movable relative to the first member during operation along a support axis defined by the interior bore;

a first stop limiting movement of the second member toward the first member along the support axis;

a second stop limiting movement of the second member away from the first member along the support axis; and a spring biasing the second member away from the first member.

3. The guard for a cast cutter as defined in claim 2, wherein the second member is generally "J" shaped with the second end of the second member forming the guard member.

4. The guard for a cast cutter as defined in claim 2, wherein the guide tracks are slots that extend through the peripheral sidewall to the interior bore.

5. The guard for a cast cutter as defined in claim 4, wherein the first end of the guide slots serves as the first stop.

6. The guard for a cast cutter as defined in claim 4, wherein the second end of the guide slots serves as the second stop.

7. The guard for a cast cutter as defined in claim 2, wherein the spring is disposed within the interior bore, the spring having a first end that bears against the first end of the first member and a second end that bears against the radial members of the second member.

\* \* \* \* \*

UNITED STATES PATENT AND TRADEMARK OFFICE
CERTIFICATE OF CORRECTION

PATENT NO. : 6,363,617 B1
DATED : April 2, 2002
INVENTOR(S) : T. Frost

It is certified that error appears in the above-identified patent and that said Letters Patent is hereby corrected as shown below:

<u>Title page,</u>
Item [30], Foreign Application Priority, insert in appropriate order
-- (30) Foreign Application Priority Data
Apr. 7, 1999 (CA) 2,268,010 --
*Primary Examiner*, "Hwei-Slu" should read -- Hwei-Siu --

Signed and Sealed this

Eighteenth Day of June, 2002

*Attest:*

*Attesting Officer*

JAMES E. ROGAN
*Director of the United States Patent and Trademark Office*